United States Patent
Thaning et al.

(10) Patent No.: US 11,186,553 B2
(45) Date of Patent: Nov. 30, 2021

(54) METAL COMPLEX FORMULATIONS

(71) Applicant: GE HEALTHCARE AS, Oslo (NO)

(72) Inventors: Mikkel Jacob Thaning, Oslo (NO); Andreas Richard Meijer, Oslo (NO)

(73) Assignee: GE HEALTHCARE AS, Oslo (NO)

( * ) Notice: Subject to any disclaimer, the term of this patent is extended or adjusted under 35 U.S.C. 154(b) by 144 days.

(21) Appl. No.: 15/531,429

(22) PCT Filed: Nov. 27, 2015

(86) PCT No.: PCT/EP2015/077958
§ 371 (c)(1),
(2) Date: May 27, 2017

(87) PCT Pub. No.: WO2016/083597
PCT Pub. Date: Jun. 2, 2016

(65) Prior Publication Data
US 2017/0266304 A1  Sep. 21, 2017

(30) Foreign Application Priority Data
Nov. 28, 2014 (GB) ..................... 1421161

(51) Int. Cl.
| | |
|---|---|
| A61K 49/10 | (2006.01) |
| C07D 257/02 | (2006.01) |
| A61K 49/18 | (2006.01) |
| A61K 47/54 | (2017.01) |
| A61K 49/00 | (2006.01) |
| A61K 31/28 | (2006.01) |

(52) U.S. Cl.
CPC .......... *C07D 257/02* (2013.01); *A61K 47/547* (2017.08); *A61K 49/0002* (2013.01); *A61K 49/101* (2013.01); *A61K 49/108* (2013.01); *A61K 49/18* (2013.01); *A61K 31/28* (2013.01); *A61K 49/106* (2013.01)

(58) Field of Classification Search
CPC ..... A61K 49/108; A61K 49/106; A61K 31/28
See application file for complete search history.

(56) References Cited

U.S. PATENT DOCUMENTS

2012/0082624 A1   4/2012   Port

FOREIGN PATENT DOCUMENTS

| | | |
|---|---|---|
| CN | 101977633 B | 8/2012 |
| EP | 2513043 A1 | 10/2012 |
| EP | 2513043 B1 | 3/2014 |
| EP | 2799090 A2 | 11/2014 |
| JP | 2013514311 A | 4/2013 |
| RU | 2512491 C2 | 4/2014 |
| WO | 2008144728 A1 | 11/2008 |
| WO | 2009103744 A2 | 8/2009 |
| WO | WO-2009103744 A2 * | 8/2009 ........... A61K 49/106 |
| WO | 2016083597 A1 | 6/2016 |

OTHER PUBLICATIONS

International Search Report and the Written Opinion of the International Searching Authority, or the Declaration from International Appl. No. PCT/EP2015/077958, dated Feb. 16, 2016.
Great Britain Search Report from GB Appl. No. GB1421161.9, dated Aug. 12, 2015.
Notification of Transmittal of The International Preliminary Report on Patentability from International Appl. No. PCT/EP2015/077958, dated Feb. 3, 2017.
Written Opinion of the International Preliminary Examining Authority from International Appl. No. PCT/EP2015/077958, dated Oct. 31, 2016.
Japan Notice of Rejection corresponding to Japanese Application No. 2017-526513, dated Jul. 23, 2019.
Russia Office Action and Search Report corresponding to Russian Application No. 2017116217/04, dated Jun. 4, 2019.
China First Office Action and Search Report corresponding the Chinese Application No. 201580064547.0, dated Nov. 11, 2019.

* cited by examiner

*Primary Examiner* — James W Rogers
(74) *Attorney, Agent, or Firm* — Jeff B. Vockrodt; Culhane Meadows, PLLC (57) ABSTRACT

The present invention relates to a method of preparation of formulations of lanthanide metal complexes of macrocyclic chelators which further comprise a small excess of free chelator. The method uses a solid phase-bound scavenger chelator to remove excess lanthanide metal ions, prior to the addition of a defined excess chelator. Also provided is a method of preparation of MRI contrast agents, together with solid-phase bound chelator meglumine salts useful in the methods.

16 Claims, 2 Drawing Sheets

METAL COMPLEX FORMULATIONS

FIELD OF THE INVENTION

The present invention relates to a method of preparation of formulations of lanthanide metal complexes of macrocyclic chelators which further comprise a small excess of free chelator. The method uses a solid phase-bound scavenger chelator to remove excess lanthanide metal ions, prior to the addition of a defined excess chelator. Also provided is a method of preparation of MRI contrast agents, together with solid-phase bound chelator meglumine salts useful in the methods.

BACKGROUND TO THE INVENTION

Metal complexes of lanthanide metals, especially gadolinium, are of interest as MRI contrast agents in the field of in vivo medical imaging. MRI contrast agents based on metal complexes of gadolinium have been reviewed extensively [see e.g. Zhang et al, Curr. Med. Chem., 12, 751-778 (2005) and Aime et al, Adv. Inorg. Chem., 57, 173-237 (2005)].

Free gadolinium ions do, however, exhibit significant toxicity in vivo. U.S. Pat. No. 5,876,695 addresses this problem by including in the formulation of the gadolinium metal complex an additive, which is a 'weak metal chelate complex' such as with calcium. The idea is that the excess 'weak metal chelate complex' will complex efficiently any gadolinium ions which may adventitiously be either liberated or present, and thus improve the safety of the MRI contrast composition.

EP 2513043 B1 discloses a method of preparation of gadolinium metal complexes in which gadolinium is first complexed to a cation exchange resin optionally functionalised with a metal coordinating group. The solid-phase bound gadolinium is subsequently reacted with an aminocarboxylic acid chelating agent to liberate the desired gadolinium complex. Any excess gadolinium remains bound to the solid-phase.

EP 2242515 B9 discloses a process for preparing a liquid pharmaceutical formulation containing a complex of macrocyclic chelate with a lanthanide and a mol/mol amount of free macrocyclic chelate of between 0.002% and 0.4%, said process comprising the following successive steps:

b) preparation of a liquid pharmaceutical composition containing the complex of macrocyclic chelate with a lanthanide, and free macrocyclic chelate that is not under the form of an excipient X[X',L] in which L is the macrocyclic chelate and X and X' are a metal ion, in particular chosen independently from calcium, sodium, zinc and magnesium, and free lanthanide, by mixing a solution of free macrocyclic chelate and of free lanthanide, so as to obtain complexation of the lanthanide by the macrocyclic chelate, the amounts of free macrocyclic chelate and of free lanthanide being such that not all the lanthanide is complexed;

c) measurement in the pharmaceutical formulation obtained in step b) of the concentration of free lanthanide $C_{lan\ 1}$; the concentration of free macrocyclic chelate $C_{ch\ 1}$ being equal to 0;

d) adjustment of $C_{ch\ 1}$ and of $C_{lan\ 1}$ by adding to the formulation obtained in step b) the amount of free macrocyclic chelate necessary, firstly, to complete the complexation of the free lanthanide so as to obtain $C_{lan\ 1}=0$, and, secondly, to obtain $C_{ch\ 1}=C_{t\ ch\ 1}$, wherein $C_{t\ ch\ 1}$ is the target concentration of the free macrocyclic chelate in the final liquid pharmaceutical formulation and is selected in the range of between 0.002% and 0.4% mol/mol, wherein the amount of free macrocyclic chelate in the final liquid pharmaceutical formulation corresponds to the proportion of free macrocyclic chelate relative to the amount of complexed macrocyclic chelate in the final liquid pharmaceutical formulation.

EP 2242515 B9 teaches that the method preferably further includes a prior step a) of determination of the theoretical target concentration of free macrocyclic chelate $C_{t\ ch\ 1}$ in the final liquid pharmaceutical formulation.

US 2012/0082624 A1 discloses a similar process to EP 2242515 B9, except that the pharmaceutical formulation is obtained in powder form.

Both EP 2242515 B9 and US 2012/0082624 A1 stress that, for an industrial scale pharmaceutical manufacturing processes, the addition of 0.1 mol % free macrocyclic chelator is difficult to achieve with the required degree of accuracy by weighing alone. That was ascribed to the 1000-fold difference in amounts of chelator involved, plus the hygroscopic nature of the chelator. The claimed invention, as described above, is to first carry out the metal complexation with an excess of lanthanide metal ion, then secondly to determine accurately the concentration of uncomplexed, excess lanthanide. That determination is subsequently used to calculate exactly how much additional chelator must be added to both complex the excess lanthanide and achieve the desired 0.1% molar excess of macrocyclic chelate.

Reference Example 3 of EP 2242515 B9 includes a laboratory scale preparation which prepares Gd-DOTA by reaction of DOTA (10 g, 25 mmol) with a stoichiometric amount of gadolinium oxide ($Gd_2O_3$, 12.5 mmol) at 80° C. in water at pH 6 to 7. The pH is then adjusted to 5, and residual free gadolinium removed by stirring with a Chelex resin for 2-hours, followed by filtration. EP 2242515 B9 teaches that the Gd-DOTA complex is then precipitated from aqueous ethanol giving an 80% isolated yield of white powder. EP 2242515 B9 does not teach how the method of Reference Example 3 can be adapted to provide the liquid pharmaceutical composition having an excess of macrocyclic chelator in the range 0.002% and 0.4% mol/mol, in particular on an industrial scale. Furthermore, the use of Chelex resin as taught by Example 3 of EP 2242515 B9 will release sodium ions, which will contaminate the product unless further purification steps are carried out. Example 3 of EP 2242515 B9 also describes the preparation of a specific gadolinium complex which necessitates purification and isolation steps unsuitable for an industrial manufacturing process of preparation of a liquid pharmaceutical formulation.

WO 2014/114664 provides a process for the preparation of Gd-DOTA meglumine (gadoterate meglumine) which first comprises the synthesis of DOTA from cyclen, followed by multi-step purification via recrystallisation and both cation and anion exchange chromatography. The purified DOTA is then reacted with $Gd_2O_3$ to give the Gd-DOTA complex, followed by the addition of meglumine to give the desired product. WO 2014/114664 does not, however, teach how to achieve the industrial scale production of a 0.1% excess DOTA.

WO 2014/161925 teaches that, when preparing Gd-DOTA and similar complexes on an industrial scale, it is necessary to assay the moisture content of the chelator prior to use and to correct the molar amounts used accordingly. WO 2014/161925 notes that the moisture content of DOTA varies with the relative humidity conditions.

There is still a need for alternative methods of preparing formulations of lanthanide metal complexes of macrocyclic chelators incorporating an excess of such chelators. The methods should preferably be suitable for pharmaceutical manufacture on an industrial scale, and also be suitable for the provision of MRI contrast agents comprising such formulations.

THE PRESENT INVENTION

The present invention provides a method of preparation of a liquid pharmaceutical formulation, said formulation comprising a metal complex of a lanthanide metal with a macrocyclic chelator, together with said chelator in uncomplexed form in an amount in the range 0.002 and 0.4 mol/mol % of said metal. Such formulations are useful in the provision of MRI contrast agents.

The present method avoids the need for the measurement and adjustment steps of the prior art, which is a useful simplification in terms of both time and effort.

The present method instead provides a method whereby the lanthanide chelator metal complex is obtained without excess lanthanide ions being present—by using a solid-phase bound scavenger chelator. Furthermore, the lanthanide chelator complex is maintained in aqueous solution, so correction for the moisture content of the complex is unnecessary. Since the process provides an intermediate solution of the lanthanide metal complex without free lanthanide ions, the amount of excess macrocyclic chelator to add to give the desired formulation having a defined excess of free chelator can be calculated readily.

The present invention also has the advantage that the lanthanide complexation and subsequent treatment with a scavenger chelator are effective in removing any impurities based on coordinated metal ions such as calcium from the chelator—by transmetallation as described below.

The method of the present invention also provides a resin-bound scavenger chelator in the meglumine salt form. This has significant advantages in that, after complexation of the lanthanide, megluminium ions as opposed to sodium ions are liberated. That has the particular advantage that the sodium ion content of the lanthanide metal complex produced is minimised.

The method of the present invention has the further advantages that it can carried out on an industrial scale, and that the resin-bound scavenger chelator can optionally be recycled after use to regenerate material suitable for manufacturing further batches of the pharmaceutical formulation.

DETAILED DESCRIPTION OF THE INVENTION

In a first aspect, the present invention provides a method of preparation of a liquid pharmaceutical formulation, said formulation comprising a metal complex of a lanthanide metal with a macrocyclic chelator, together with said chelator in uncomplexed form in an amount in the range 0.002 and 0.4 mol/mol % of said metal complex, said process comprising the following steps:
  (i) complexation of said chelator with an excess of said lanthanide metal in a suitable solvent, to give a first solution of said metal complex containing excess lanthanide;
  (ii) removal of the excess lanthanide from the first solution of step (i) by contacting said solution one or more times with a solid-phase bound scavenging chelator, whereby the excess lanthanide is complexed to said scavenging chelator;
  (iii) separation of the solid phase from the first solution of step (ii), to give a second solution which comprises said metal complex free from excess lanthanide;
  (iv) addition of said chelator in uncomplexed form in the range 0.002 and 0.4 mol/mol % to said second solution from step (iii) to give said liquid pharmaceutical formulation;

wherein said chelator in uncomplexed form is free of coordinated metal ions. The terms "chelator" or "chelating agent" have their conventional meaning, and refer to ligands which form coordination metal complexes which comprise multiple metal donor atoms arranged such that typically 5-, 6- or 7-membered chelate rings (preferably 5- or 6-membered such rings) result upon coordination (by having a non-coordinating backbone of either carbon atoms or non-coordinating heteroatoms linking the metal donor atoms). The term "macrocyclic" has its conventional meaning in the field of coordination chemistry, and refers to a chelator where at least some of the metal donor atoms of said chelator are covalently linked as part of a ring system.

The phrase "chelator in uncomplexed form" refers to the 'free chelator', i.e. without any coordinated metal ions. Hence, the chelator in uncomplexed form does not have any coordinated lanthanide or other metal ions, and is thus fully available for subsequent metal complexation. The 'chelator in uncomplexed form' may contain metal ions in ionic form, such as when present as salts of metal donor group, e.g. of a carboxylic acid.

The phrase "solid-phase bound scavenging chelator" refers to a chelating agent covalently conjugated to a solid phase material insoluble in the solvent used for lanthanide complexation. The conjugated chelator complexes free metal ions in solution, and is thus capable of removing or 'scavenging' any such metal ions from solution. The scavenger chelator is chosen to be different from the 'macrocyclic chelator', and hence suitably has a lower formation constant for the lanthanide metal than the 'macrocyclic chelator', and is suitably chosen so that it cannot displace the lanthanide metal ion from the lanthanide metal complex of the macrocyclic chelator of the present claims. The scavenger chelator is preferably chosen such that the kinetics of capturing a free metal ion in solution are rapid. For that reason, linear (i.e. non-macrocyclic) scavenger chelators are preferred. Being bound to a solid phase, the scavenger chelator is easily separated from the solution it is in contact with by filtration, with optional washing. Suitable solid phase materials include synthetic polymers and copolymers.

The method of Example 3 of EP 2242515 B9 has the problem that sodium ions would be released. Such sodium ions would add to the osmolality of the liquid pharmaceutical formulation. That is undesirable for intermediate solutions or compositions used in contrast agent manufacture, because high osmolality contrast agents are linked to soft tissue oedema, inflammation and tissue damage [Cohan et al, Radiology, 200(3), 593-604. doi:10.1148/radiology.200.3.8756899 (1996)]. A contrast agent production process should therefore not introduce ionic species that will affect the osmolality of the product.

In the case of DOTA, it is known that the sodium salt of gadoteric acid is prone to crystallization [Chang et al, Inorg. Chem., 32(16), 3501-3508 (1993)], hence it is important to keep sodium levels as low as possible in order to minimise the risk of GdDOTA-meglumine precipitating as NaGdDOTA.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

Suitable solvents for the complexation of step (i) are known in the art [*The Chemistry of Contrast Agents in Medical Magnetic Resonance Imaging*, 2$^{nd}$ Edition, A.Merbach, L.Helm & E.Toth (Eds), Wiley (2013)], and are preferably aqueous. The complexation of lanthanides by macrocyclic chelators (e.g. DOTA) is a multistep process that involves a somewhat stable initial complex that slowly matures to give the final, thermodynamically stable metal complex. In step (i), it is preferred to ensure that said stable lanthanide complex has been generated, as is known in the art [Moreau et al, Chem. Eur. J., 10(20), 5218-32 (2004)] —e.g. by heating, prolonged reaction times, raising the pH, or combinations thereof, before proceeding to step (ii).

The excess of lanthanide metal in step (i) is obtained by calculation of the molar ratios knowing the stoichiometry of the lanthanide macrocyclic chelator metal complex. That is typically a 1:1 complex. Such information is given in *The Chemistry of Contrast Agents in Medical Magnetic Resonance Imaging*, 2$^{nd}$ Edition, A.Merbach, L.Helm & E.Toth (Eds), Wiley (2013); for gadolinium complexes by Port et al [Biometals, 21, 469-490 (2008)]; and for DOTA complexes by Viola-Villegas et al [Coord. Chem. Rev., 253, 1906-1925 (2009)]. The percentage chemical purity of both the lanthanide used and the chelator in question are also taken into account.

The contacting of step (ii) is suitably carried out such that the whole of the 'first solution' is exposed to the Chelex resin. This can be carried out by two principal methods, or combinations thereof. The first option is to mix the solid phase resin with the 'first solution'. Alternatively, the solid phase can be provided as a column, and the 'first solution' eluted through the column. This is not a chromatographic method as such, but a convenient way of exposing the 'first solution' to the Chelex resin. The separation of step (iii) is then achieved by either filtration of the solution to remove the lanthanide-bound resin, or by collecting the eluate from the column elution respectively. For either option, the 'first solution' can be exposed to the Chelex resin multiple times. Preferably, either the filtered resin or solid phase column can be washed with a suitable solvent to ensure more complete recovery of the 'second solution'.

The addition of step (iv) is preferably carried out without a prior, in-process assay of the concentration/amount of free lanthanide in either the first or second solutions.

That is because such a step is unnecessary for the present method—the removal and separation of steps (ii) and (iii) gives the 'second solution' with a known (i.e. effectively zero) concentration of free lanthanide. Hence, the addition of step (iv) is carried out on the basis of a calculated amount of 'chelator in uncomplexed form' based on an assumed 100% conversion in the complexation reaction of step (i), based on the starting molar amount of macrocyclic chelator in step (i). That 100% conversion is in accord with what is known in the art on the efficiency of such reactions. The free chelator can be added either as a solid, or as a solution and preferably as a solution. When a solution of the macrocyclic chelator is prepared in order to carry out step (i), then a most preferred method is to remove a suitable volume fraction from that solution prior to the addition of the lanthanide (e.g. removing ca. 1L from a 1000L reaction volume or equivalent). This volume fraction is then conveniently used for the addition of step (iv). This approach obviates the need to make up multiple solutions, and/or to carry out multiple calculations to correct for purity or water content.

The method of the first aspect is suitable for carrying out on a laboratory, pilot plant or industrial manufacture scale. The method is particularly suitable for kilogramme scale production from 1 kg to 800 kg, preferably 100 kg to 650 kg scale.

The method of the first aspect has the advantage that, as part of the process, many coordinated impurity metals (such as calcium), present in the macrocyclic chelator (e.g. DOTA), as calcium-DOTA complexes will be displaced by the gadolinium, and then removed by the subsequent scavenger chelator treatment of steps (ii) and (iii). Thus, the excess lanthanide of step (i) preferably also displaces any coordinated impurity metals from said chelator, wherein said displaced impurity metal has a lower formation constant with said macrocyclic chelator than said lanthanide. That is because, as described above, the lanthanide complexation is carried out under 'thermodynamic conditions' such that the thermodynamic product is obtained—the lanthanide metal complex.

This has the advantage that it obviates the need for an additional macrocyclic chelator purification step. Thus, the excess lanthanide induces a transmetallation reaction, as illustrated in Scheme 1 for Ca-DOTA and gadolinium ions:

Scheme 1. Transmetallation of CaDOTA to generate free calcium ions

The slight excess of gadolinium will ensure complete complexation of the DOTA to give Gd-DOTA, and DOTA-coordinated impurity metal ions (such as calcium) can effectively be transmetallated into solution as free ions by virtue of a less favourable thermodynamic stability.

See Table 1 for a list of various DOTA-metal ion complexes and their thermodynamic stability:

TABLE 1

Thermodynamic stability constants for various DOTA complexes.

| Metal ion | DOTA Thermodynamic Stability Constant* |
|---|---|
| $Fe^{3+}$ | 29.4 |
| $Dy^{3+}$ | 24.8 |
| $Gd^{3+}$ | 24.7 |
| $Tm^{3+}$ | 24.4 |
| $Eu^{3+}$ | 23.5 |
| $Pr^{3+}$ | 23.0 |
| $La^{3+}$ | 22.9 |
| $Cu^{2+}$ | 22.3 |
| $Zn^{2+}$ | 20.8 |
| $Mn^{2+}$ | 20.0 |
| $Ca^{2+}$ | 17.2 |
| $Mg^{2+}$ | 11.85 |
| $Na^+$ | 4.2 |
| $K^+$ | 1.60 |

*Data from:
[1]Popov, K. Felcman, J. Delgado, R. Arnaud-Neu, F. Anderegg, G. Pure Appl. Chem. 77, 8, 2005
[1]Cacheris, W. P, Nickle, S. K. Sherry, A. D; Inorg. Chem. 2646, 1986.
[1]Toth, E. Brucher, E; Inorganica Chimica Acta, 221(1-2), 1994, pp. 165-167.

Hence, any coordinated metal ions having a lower stability constant than Gd-DOTA (such as calcium, manganese, zinc, copper or magnesium), would be liberated by Gd transmetallation, and then removed by the scavenger chelator in steps (ii) and (iii).

PREFERRED EMBODIMENTS

In the method of the first aspect, the excess of lanthanide metal of step (i) is preferably 0.01 to 5, more preferably 0.01 to 1, most preferably 0.05 to 0.5 mol/mol %.

When a Chelex-100 resin is used, the Chelex resin has a higher affinity for gadolinium than calcium. That means that the use of a great excess of gadolinium in the complexation reaction of step (i) will lead to a less efficient scavenging process, because a great excess of scavenger resin would need to be added—firstly to remove the free gadolinium and secondly remove free calcium (or similar metal ions). It is therefore advantageous to use a very low excess of gadolinium in the complexation reaction of step (i).

If the macrocyclic chelator is believed to contain coordinated calcium or similar metal ions as described above, then a very low excess of gadolinium in the range (ca. 0.01 to 0.1 mol % or 10-100 ppm in a 0.5M GdDOTA solution) is preferred. Such a range is low enough to ensure enough scavenger capacity for calcium (metal) removal, but high enough to ensure complete transmetallation of any Ca-DOTA complex (or related species).

The lowest levels within this range (ca. 0.01 to 0.1 mol %) of excess lanthanide metal can be achieved by incremental addition of aliquots of such lanthanide until a positive test for the presence of free lanthanide ions is observed. Such "spot tests" give a yes/no answer to the presence/absence question, but do not provide information on the concentration of free lanthanide. The spot tests can be carried out using visual colouration using xylenol orange as is known in the art [Barge et al, Contrast Med. Mol. Imaging, 1, 184-188 (2006). Barge et al teach that visual detection of the orange coloration indicative of free $Gd^{3+}$ is effective to detect $Gd^{3+}$ at concentrations down to 10 µM or less. Alternatively, for gadolinium, the excess gadolinium can be determined by xylenol orange assay or Arsenazo III assay as is known in the art [Barge et al, Contrast Med. Mol. Imaging, 1, 184-188 (2006) and Clogston et al, Molec. Biol., 697, 101-108 (2011) respectively]. Xylenol orange and Arsenazo III are commercially available, from e.g. Sigma-Aldrich. If the spot test indicates the lack of free gadolinium, then additional gadolinium can be added. The higher levels (>0.1 mol % up to 5 mol %), of excess lanthanide can be achieved by weighing alone.

In the method of the first aspect, the chelator in uncomplexed form is preferably in an amount in the range 0.025 and 0.25, more preferably 0.05 to 0.20, most preferably 0.10 to 0.15 mol/mol % relative to the macrocyclic lanthanide complex. The chelator in uncomplexed form is suitably free of lanthanide metal ions, and is preferably also free of coordinated calcium, zinc and magnesium ions.

In the method of the first aspect, the lanthanide metal is preferably gadolinium praseodymium, dysprosium, europium or thulium, and is most preferably gadolinium.

The macrocyclic chelator is preferably heptadentate or octadentate, and more preferably comprises N and/or O donor atoms. The donor atoms are preferably provided by: carboxylate, amine, alcohol or phosphonate donor groups. The macrocyclic chelator is more preferably of the aminocarboxylic acid type. When the macrocyclic chelator is of the aminocarboxylic class, such chelators preferably comprise: DOTA, NOTA, DO3A, BT-DO3A, HP-DO3A or PCTA. The macrocyclic chelator most preferably comprises DOTA, or a salt thereof:

DOTA

DOTA and its' metal complexes in biomedical imaging have been described by Stasiuk and Long [Chem. Comm, 49, 2732-2746 (2013)].

In the method of the first aspect, it is preferred that the lanthanide metal is gadolinium and the macrocyclic chelator comprises DOTA. Most preferably, the gadolinium-DOTA complex comprises the meglumine salt of gadolinium-DOTA.

The scavenger chelator preferably comprises iminodiacetic acid (IDA), EDTA or DTPA, more preferably iminodiacetic acid. A preferred solid-phase bound scavenging chelator is Chelex® 100, which is a styrene divinylbenzene copolymer, having conjugated thereto the chelator IDA. Chelex® 100 is commercially available in either the sodium or ammonium salt form from Bio-Rad Laboratories. The commercial supplier provides information on suitable amounts of resin to use for a given amount of metal to remove. At neutral pH, Chelex functions as a cation exchange resin, so has no affinity for lanthanide metal complexes which are negatively charged such as Gd(DOTA). That has the advantage that there is minimal non-specific binding of such complexes to the solid phase, and hence minimal impact on yield.

The scavenging chelator is preferably present as the meglumine salt of said scavenging chelator. Such materials are described in the third aspect (below).

The lanthanide complexation process of step (i) is typically multistep in nature. For gadolinium, firstly a low pH (pH ca. 2) is required to dissolve all the $Gd_2O_3$ to give free gadolinium ions in solution. At this low pH, the carboxylate groups of aminocarboxylate chelators (e.g. DOTA) are unable to fully complex all the gadolinium ions because the carboxylate groups are partially protonated. The pH is then raised (to ca. pH 4 to 5) by the addition of base (preferably meglumine), to favour formation of the carboxylate anion, which in turn favours metal complexation. The initial Gd-DOTA complex formed is actually bis-protonated, then slowly matures to give the final Gd-DOTA complex of high thermodynamic (and kinetic) stability

[Moreau et al, Chem. Eur. J., 10(20), 5218-5232 (2004)]. The maturation process is favoured by a higher pH and heating (typically a few hours at ca. pH 5 with heating completes the reaction). Preferably, a pH in excess of 7 is avoided, since that risks causing hydrolysis of any gadolinium ions, with subsequent re-formation of $Gd_2O_3$.

When the lanthanide metal complex of the first aspect is to be obtained as a meglumine salt, the complexation of step (i) is preferably completed by adjusting the pH to 4.5 to 5.5 using meglumine The removal of step (ii) is preferably carried out at pH 4.0 to 6, more preferably 4.5 to 5.5, with ca. pH 5 being the ideal.

The addition of step (iv) is preferably carried out by first adding the excess chelator, then neutralising to neutral pH (ca. pH 7.0-7.4). When the desired lanthanide macrocyclic complex is a meglumine salt, this neutralisation is preferably carried out using meglumine The macrocyclic chelators of the invention are commercially available from a range of suppliers. DOTA can also be synthesised by the method of Desreux [Inorg.Chem., 19, 1319-1324 (1980)1. Further details on macrocyclic chelator syntheses are given by Kotel et al [Chapter 3 pages 83-155 in *The Chemistry of Contrast Agents in Medical Magnetic Resonance Imaging*, $2^{nd}$ Edition, A.Merbach, L.Helm & E.Toth (Eds), Wiley (2013)].

Meglumine (N-methylglucamine) is commercially available from a range of suppliers. Preferably, pharmaceutical grade material is used.

In a second aspect, the present invention provides a method of preparation of an MRI contrast agent which comprises:
 (a) carrying out the method of the first aspect to obtain the liquid pharmaceutical formulation as defined therein;
 (b) optionally diluting the liquid pharmaceutical formulation from step (a) with a biocompatible carrier;
 (c) dispensing the formulation from step (b) into pharmaceutically acceptable containers or syringes to give dispensed containers or syringes;
 (d) either carrying out steps (a)-(c) under aseptic manufacturing conditions, or terminal sterilisation of the dispensed containers or syringes from step (c), to give the MRI contrast agent in said pharmaceutically acceptable containers or syringes in a form suitable for mammalian administration.

Preferred embodiments of the liquid pharmaceutical formulation, lanthanide, macrocyclic chelator and method of step (a) in the second aspect are as described in the first aspect (above).

The term "contrast agent" has its' conventional meaning in the field of in vivo medical imaging, and refers to an agent in a form suitable for mammalian administration, which assists in providing clearer images in the region or organ of interest than could be obtained by imaging the subject alone. An "MRI contrast agent" is typically a paramagnetic or ferromagnetic substance, suitable for mammalian administration, which shortens the T1 and/or T2 relaxation time of the relevant nuclei (e.g. $^1H$ for $^1H$ NMR) in the region of interest for imaging within the subject.

By the term "subject" is meant a mammal in vivo, preferably the intact mammalian body in vivo, and more preferably a living human subject. By the phrase "in a form suitable for mammalian administration" is meant a composition which is sterile, pyrogen-free, lacks compounds which produce toxic or adverse effects, and is formulated at a biocompatible pH (approximately pH 4.0 to 10.5). Such compositions lack particulates which could risk causing emboli in vivo, and are formulated so that precipitation does not occur on contact with biological fluids (e.g. blood). Such compositions also contain only biologically compatible excipients, and are preferably isotonic.

As with other in vivo imaging agents, the contrast agent is designed to have minimal pharmacological effect on the mammalian subject to be imaged. Preferably, the contrast agent can be administered to the mammalian body in a minimally invasive manner, i.e. without a substantial health risk to the subject when carried out under professional medical expertise. Such minimally invasive administration is preferably intravenous administration into a peripheral vein of said subject, without the need for local or general anaesthetic.

By the term "biocompatible carrier" is meant a fluid, especially a liquid, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). Preferably the biocompatible carrier is pyrogen-free water for injection (WFI), isotonic saline or phosphate buffer.

The phrase "aseptic manufacture" refers to carrying out the relevant process steps under aseptic manufacture, i.e. apyrogenic conditions, e.g. in a clean-room environment. The terms "sterilising" or "sterilisation" have their conventional meaning, and refer to a process of destruction of micro-organisms, to obtain a sterile, pyrogen-free composition. The phrase "terminal sterilisation" has its conventional meaning, and refers to carrying out the preceding steps to GMP (Good Manufacturing Practice), but carrying out the sterilisation step as late as possible in the overall process. The components and reagents can be sterilised by methods known in the art, including: sterile filtration, terminal sterilisation using e.g. gamma-irradiation, autoclaving, dry heat or chemical treatment (e.g. with ethylene oxide) or combinations thereof. The term "autoclaving" has its' conventional meaning, and refers to one particular method of sterilisation which uses superheated steam to sterilise. Autoclaving and other sterilisation methods are described in *Achieving Sterility in Medical and Pharmaceutical Products*, N.Halls (CRC Press, 1994). In the method of the second aspect, terminal sterilisation is preferred. A preferred method of terminal sterilisation is autoclaving.

The term "dispensed container or syringe" refers to a charged container, i.e. a container into which has been dispensed an aliquot of the composition, i.e. a dispensed vial.

Suitable containers, vials and closures and syringes for use in the method of the second aspect are pharmaceutical grade and are widely available commercially.

In a third aspect, the present invention provides a solid-phase bound scavenging chelator, where the solid-phase bound scavenging chelator is present as the meglumine salt of said scavenging chelator.

Preferred embodiments of the solid-phase bound scavenging chelator of the third aspect, are as described in the first aspect (above). The solid-phase bound scavenging chelator of the third aspect preferably comprises iminodiacetic acid (IDA).

When the scavenger chelator is used as the meglumine salt, such materials can be prepared by conventional ion exchange chromatography techniques, to change the counter-ion (e.g. the sodium or ammonium salts of Chelex®-100), by incubation or elution with excess meglumine solution. The solid phase may then optionally have the moisture content reduced before use, but is suitably used in moist form.

Alternatively, the megluminium scavenger resin could be generated in situ, by adding the protonated form of the resin (obtained by washing e.g. commercial Chelex with a strong acid in a similar procedure to that of Example 1). The hydroxonium Chelex resin will then form the corresponding megluminium form in situ in the complexation reaction mixture, containing meglumine Such meglumine resins have the particular advantage that, when preparing meglumine salts of the lanthanide metal complex, the sodium ion/salt content of the product is reduced. Thus, the counter-ion of the scavenger chelate (IDA) in the commercial Chelex® resin is sodium, and hence for every gadolinium ion that is captured, three sodium ions are released into the reaction mixture. To avoid sodium contamination, the Chelex® resin can be prepared so that all sodium ions are exchanged for megluminium ions. Consequently, when a gadolinium ion is captured by the scavenger resin, three megluminium ions are released.

After use, the scavenger chelate resin having bound metal ions may optionally be regenerated for subsequent re-use by treatment with an excess of meglumine or other counter-ion. For Chelex, standard regeneration methods are described in the instruction manual provided by the commercial supplier. The complete removal of gadolinium would be determined by ICP-AES or ICP-MS of the eluate after aqueous acidic washes of the resin, or by the 'spot-tests' referred to above.

In a fourth aspect, the present invention provides the use of the solid-phase bound scavenging chelator of the third aspect in the method of preparation of a pharmaceutical formulation of the first aspect, or the method of preparation of an MRI contrast agent of the second aspect.

Preferred embodiments of the solid-phase bound scavenging chelator of the fourth aspect, are as described in the first aspect (above).

DESCRIPTION OF THE FIGURES

FIG. 2 also demonstrates that chelex is unable to remove gadolinium from Gd-DOTA, as no free DOTA is formed.

Figure 1:
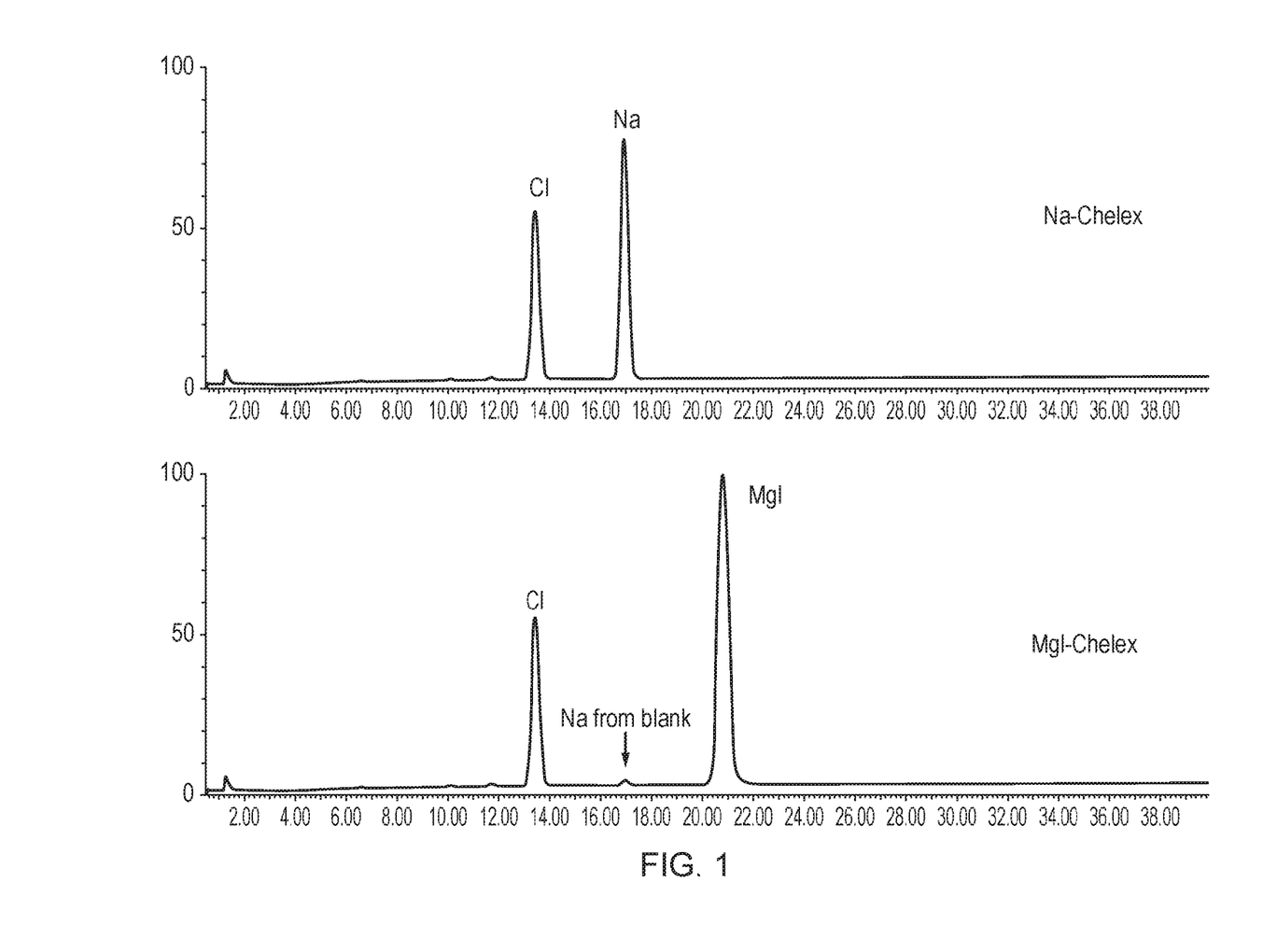
FIG. 1 shows that gadolinium ions are replaced with either sodium (Na-Chelex) or megluminium ($M^{eg}$-Chelex) ions, and the chloride ion content is unaffected by treatment of a gadolinium chloride reference solution with the Chelex resins.

The invention is illustrated by the non-limiting Examples detailed below. Example 1 provides the preparation of a meglumine scavenger chelator resin according to the invention. Example 2 shows that two different Chelex resins successfully remove gadolinium ions from a reference solution of $GdCl_3$. The sodium form of the resin is shown to increase the sodium content of the solution and the megluminium form of the resin is shown to increase the megluminium content of the solution.

Figure 2:
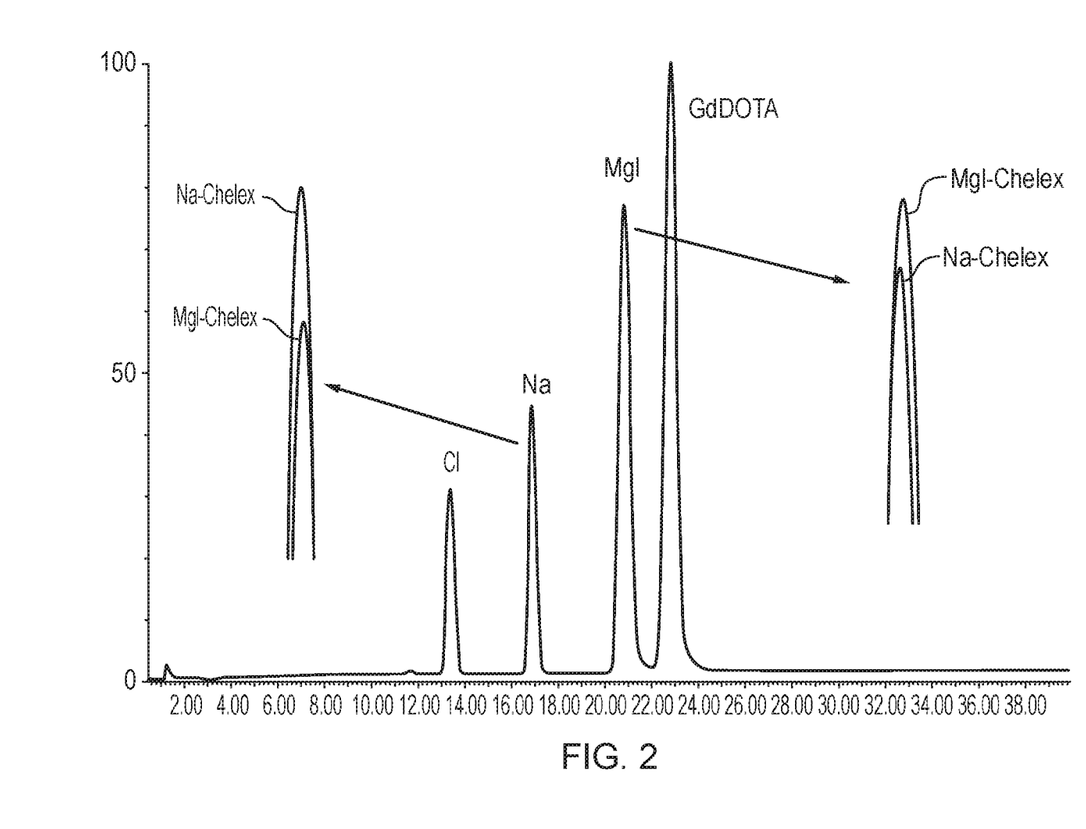
FIG. 2 shows that the same gadolinium removal procedure of the invention is effective when used on a mixture of Gd-DOTA/excess gadolinium.

Example 3 shows that the two different Chelex resins of Example 2 successfully remove gadolinium ions from a composition containing the Gd-DOTA complex with excess free gadolinium. Example 3 also demonstrates that the Chelex resin is unable to remove $Gd^{3+}$ from the Gd-DOTA complex, because no free DOTA is present in the chromatogram (FIG. 2).

Example 4 provides a HPLC-CAD method capable of analysing Gd-DOTA, free DOTA and meglumine in a mixture of such components.

Example 5 provides the synthesis of a Gd-DOTA complex formulation containing excess DOTA according to the invention.

Example 6 provides a method for the megluminization of a scavenger resin, according to the invention.

ABBREVIATIONS

BT-DO3A: 10-(2,3-dihydroxy-1-hydroxymethylpropyl)-1,4,7,10-tetraazacyclododecane-1,4,7-triacetic acid;
Cyclen: 1,4,7,10-tetraazacyclododecane;
DO3A: 1,4,7,10-tetraazacyclododecane-1,4,7-triacetic acid;
DOTA: 1,4,7,10-tetraazacyclododecane-1,4,7,10-tetraacetic acid;
DTPA: diethylenetriamine-pentaaacetic acid;
EDTA: ethylenediamine-tetraacetic acid;
GMP: Good Manufacturing Practice;
HP-DO3A: 1,4,7,10-tetraazacyclododecane-1,4,7-triacetic acid-10-(2-hydroxypropyl);
HPLC: High Performance Liquid Chromatography;
HPLC-CAD: HPLC Charged Aerosol Detector;
ICP-AES: Inductively Coupled Plasma Atomic Emission Spectroscopy
ICP-MS: Inductively Coupled Plasma Mass Spectrometry;
MeCN: Acetonitrile;
min: minutes;
MRI: Magnetic Resonance Imaging;
NOTA: 1,4,7-Triazacyclononane-1,4,7-triacetic acid;
PCTA: 3,6,9,15-tetraazabicyclo[9.3.1]pentadeca-1,11,13-triene-3,6,9,-triacetic acid;
WFI: water for injection.

EXAMPLE 1

Preparation of Megluminized Chelex® Resin ("Meg-Chelex")

Chelex-100 resin (Sigma-Aldrich; 100 g) on a sintered glass filter was treated with 1M HCl (1 L) in 4 portions over 4 h. The resin was then washed with water until the eluent was pH 6.5, and a solution of meglumine (10 g) in water (400 mL) was equilibrated with the resin over a period of 1 h. The resin was again washed with water to pH 8, and then filtered and dried under vacuum for a minute to give the moist resin, which is used in this form ("$M^{eg}$-Chelex").

EXAMPLE 2

Removal of Gadolinium Ions Using Chelex® Resin

A gadolinium chloride reference solution was treated with either standard Chelex (sodium ion form; "Na-Chelex" or megluminized Chelex (Example 1; "$M^{eg}$-Chelex"): To each moist Chelex (Na or meglumine) resin (0.5 g) was added 5 mL of a $GdCl_3$ reference solution (1 mg/mL). The suspension was then left on a shaking table overnight at 30° C. HPLC-CAD analysis (using the method of Example 4) of the suspensions indicated that there was no sodium contamination of the gadolinium solution treated with $M^{eg}$-Chelex, whereas the solution treated with Na-Chelex had a much higher sodium ion concentration. Arsenazo dye testing indicated no free gadolinium in either solution (the limit of detection using this method is 8 ppm). The results are shown in FIG. 1.

EXAMPLE 3

Removal of Gadolinium Ions from a Gd-DOTA/Excess DOTA Preparation Using Chelex® Resin A Gd-DOTA-meglumine reaction mixture (concentration ~380 mg/mL) containing a known excess of free gadolinium (160 µg/mL) was treated with standard (Na-Chelex) or megluminized ($M^{eg}$-Chelex) Chelex:

To 0.5 g of the moist Chelex resin (Na-Chelex or $M^{eg}$-Chelex; Example 1), was added a 5 mL aliquot of the above Gd-DOTA-meglumine/free Gd mixture. The suspension was left on a shaking table overnight at 30° C.

HPLC-CAD analysis (using the method of Example 4) of the resulting suspensions indicated no additional sodium contamination (DOTA containing some sodium ions was used) of $M^{eg}$-Chelex treated gadolinium solution, whereas Na-Chelex treated solution had increased levels of sodium. Arsenazo dye testing indicated no free gadolinium in either solution. The meglumine concentration in the $M^{eg}$-Chelex treated reaction mixture was slightly increased, indicative of gadolinium exchange. The results are shown in FIG. 2.

EXAMPLE 4

HPLC-CAD Method: DOTA Determination in GdDOTA-Meglumine Solution

Detector: ESA Corona, Charged Aerosol Detector;
Column: SeQuant ZIC-pHILIC (5 µm, 150*4.6 mm).
Sample preparation: to 20 µL (ca 0.5M) reaction mixture was added $Zn(OAc)_2$ (10 µg/mL) then water (270 µL) followed by MeCN (700 µL)*.
Injection volume: 20 µL;
Mobile phase: 100 mM ammonium acetate (A), Acetonitrile (B).

The column was conditioned with an initial composition (of 15:85 A:B) at a flow rate of 1 mL/min for at least five minutes prior to sample injection.
Gradient:

| | Time (min) | Flow Rate (mL/min) | % A | % B | Curve |
|---|---|---|---|---|---|
| 1. | initial | 1.00 | 15.0 | 85.0 | |
| 2. | 50.00 | 1.00 | 33.0 | 66.0 | 6 | where curve 6 refers to a linear gradient.
The following retention times were observed:

| | Retention time (min) |
|---|---|
| Meglumine | 21.3 |
| GdDOTA | 23.2 |
| ZnDOTA* | 28.1. |

*DOTA was analysed indirectly as the ZnDOTA complex.

EXAMPLE 5

Preparation of a Gd-DOTA Complex Formulation Containing Excess DOTA

DOTA (211 kg) was dissolved in boiling water (1600 kg) and $Gd_2O_3$ was added (94.8 kg). The temperature was set to 70° C. and the slurry was stirred over-night. The presence of free gadolinium ions (1390 ug/g) in the solution was determined by colorimetric titration.

The temperature was adjusted to 50° C. and meglumine was added to achieve pH 5.5 in the solution. Initially 94.8 kg meglumine was added and the final adjustment of the pH was made with an aqueous solution of meglumine (1.5 M).

Scavenger resin (Puropack C150, 50 L, preconditioned according to example 6) was placed in a column. The GdDOTA solution was pumped through the column at a flow rate sufficient to pass the entire volume of solution in 2 h. The concentration of free gadolinium (45 ug/ml) was determined using colorimetric titration. The ion exchange of the GdDOTA solution was continued with one more passage through the column to establish a level of free gadolinium below detection limit by colorimetric titration (4 ug/g), to give a GdDOTA-meglumine solution.

An aliquot of the purified GdDOTA-meglumine complexation mixture was treated to an additional process step: The concentration of GdDOTA was determined by IR measurement and together with a weight measurement of the solution, the total amount of GdDOTA was determined to be 269.8 kg. Free DOTA (2.79 litre of 101.1g/mL solution; total of 307.6g) was then added.

Then Meglumine solution (1 M) was added in small portions until a pH of 7.2 was obtained. The weight was reduced to 630 kg by distillation in vacuo (140° C.). The solution was kept at 40° C. for 10 h. The concentration of GdDOTA was determined to 1.06M, and the amount of free DOTA was determined to 537 ug/mL.

EXAMPLE 6

Preparation of Megluminized Puropack C150® Resin ("$M^{eg}$-PPC")

Puropack C150 resin was conditioned to proton form according to standard procedures. The resin was rinsed with water until neutral water was eluted from the resin bed.

A solution of meglumine (400 g/kg resin) was cycled through the resin bed for 10h and the resin was again rinsed to neutral pH with water.

The invention claimed is:

1. A method of preparation of a liquid pharmaceutical formulation, said formulation comprising a metal complex of a lanthanide metal with a macrocyclic chelator, together with said chelator in uncomplexed form in an amount in the range 0.002 and 0.4 mol/mol % of said metal complex, said method comprising:
   (i) complexing said chelator with an excess of said lanthanide metal in a suitable solvent, to give a first solution of said metal complex containing excess lanthanide;
   (ii) removing the excess lanthanide from the first solution of step (i) by contacting said solution one or more times with a scavenger resin, wherein said scavenger resin used for contacting said solution is a solid-phase bound scavenger chelator present as the meglumine salt of said scavenging chelator, whereby the excess lanthanide is complexed to said scavenger resin and exchanged for cationic meglumine counter-ions;
   (iii) separating the solid phase from the first solution of step (ii), to give a second solution which comprises said metal complex free from excess lanthanide;
   (iv) adding said chelator in uncomplexed form in the range 0.002 and 0.4 mol/mol % to said second solution from step (iii) to give said liquid pharmaceutical formulation;
wherein said chelator in uncomplexed form is free of coordinated metal ions.

2. The method of claim 1, wherein the excess of lanthanide metal of step (i) is 0.001 to 5 mol/mol %.

3. The method of claim 1, wherein the chelator in uncomplexed form is in an amount in the range 0.025 and 0.25 mol/mol.

4. The method of claim 1, wherein the chelator in uncomplexed form is free of lanthanide, calcium, zinc and magnesium ions.

5. The method of claim 1 wherein the lanthanide metal is gadolinium.

6. The method of claim 1, wherein the macrocyclic chelator comprises DOTA, NOTA, DO3A, BT-DO3A, HP-DO3A and PCTA.

7. The method of claim 6, wherein the macrocyclic chelator comprises DOTA.

8. The method of claim 1, wherein the scavenger chelator comprises iminodiacetic acid, EDTA or DTPA.

9. The method of claim 8, wherein the scavenger chelator comprises iminodiacetic acid.

10. The method of claim 1 wherein the excess lanthanide of step (i) displaces any coordinated impurity metal(s) from said chelator, wherein each said impurity metal has a lower formation constant with said macrocyclic chelator than said lanthanide.

11. The method of claim 1, wherein the lanthanide metal is gadolinium and the macrocyclic chelator comprises DOTA.

12. The method of claim 11, wherein the gadolinium-DOTA complex comprises the meglumine salt of gadolinium-DOTA.

13. The method of claim 12, wherein the scavenger chelator comprises iminodiacetic acid.

14. The method of claim 1, wherein the complexation of step (i) is completed by adjusting the pH 4.5 to 5.5 using meglumine.

15. A method of preparation of an MRI contrast agent, the method comprising:
   (a) carrying out the method of claim 1 to obtain the liquid pharmaceutical formulation as defined therein;
   (b) optionally diluting the liquid pharmaceutical formulation from step (a) with a biocompatible carrier;
   (c) dispensing the formulation from step (b) into pharmaceutically acceptable containers or syringes to give dispensed containers or syringes;
   (d) either carrying out steps (a)-(c) under aseptic manufacturing conditions, or terminal sterilisation of the dispensed containers or syringes from step (c), to give the MRI contrast agent in said pharmaceutically acceptable containers or syringes in a form suitable for mammalian administration.

16. The method of claim 15, wherein terminal sterilisation is used.

* * * * *